US00PP33079P2

(12) United States Plant Patent
Lock

(10) Patent No.: US PP33,079 P2
(45) Date of Patent: May 18, 2021

(54) ***HAWORTHIA* PLANT NAMED 'LOCK02'**

(50) Latin Name: *Haworthia limifolia*
Varietal Denomination: LOCK02

(71) Applicant: Handelskwekerij Lock VOF, 's-Gravenzande (NL)

(72) Inventor: Pieter Lock, 's-Gravenzande (NL)

(73) Assignee: Handelskwekerij Lock VOF, 's-Gravenzande (NL)

( * ) Notice: Subject to any disclaimer, the term of this patent is extended or adjusted under 35 U.S.C. 154(b) by 0 days.

(21) Appl. No.: 16/906,216

(22) Filed: Jun. 19, 2020

(30) Foreign Application Priority Data

Nov. 13, 2019 (QZ) ..... PBR 2019/2965

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

*Primary Examiner* — Anne Marie Grunberg
(74) *Attorney, Agent, or Firm* — Samuel R. McCoy, Jr.

(57) ABSTRACT

A new and distinct *Haworthia* plant named 'LOCK02', which is characterized by spirally-arranged, light green foliage which is densely covered with prominent linear protuberances presenting as white raised ribs which transversely encircle both the adaxial and abaxial leaf surfaces. The new variety has shown to be uniform and stable in the resulting generations from asexual propagation.

4 Drawing Sheets

Latin name of the genus and species: The Latin name of the genus and species of the novel variety disclosed herein is *Haworthia limifolia.*

Variety denomination: The inventive variety of *Haworthia* hybrid disclosed herein has been given the variety denomination 'LOCK02'.

CROSS REFERENCE TO RELATED APPLICATIONS

This application claims priority to the Community Plant Variety Rights application number 2019/2965, filed Nov. 13, 2019, which is herein incorporated by reference.

BACKGROUND OF THE INVENTION

Parentage: 'LOCK02' is a spontaneous whole-plant mutation of *Haworthia limifolia* 'LOCK01' (Community Plant Variety Rights grant number 28557) which was discovered in the spring of 2010 at a commercial greenhouse in 's-Gravenzande, the Netherlands. The mutation was noted for its light green foliage with prominent white ribs encircling the leaves.

Asexual Reproduction: Asexual reproduction of the new cultivar 'LOCK02', by way of meristematic tissue culture, was first initiated in the spring of 2010 at the inventor's commercial greenhouse in 's-Gravenzande, the Netherlands. Through three subsequent generations, the unique features of this cultivar have proven to be stable and true to type.

SUMMARY OF THE INVENTION

The cultivar 'LOCK02' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LOCK02'. These characteristics in combination distinguish 'LOCK02' as a new and distinct *Haworthia* cultivar:

1. 'LOCK02' exhibits thick, succulent foliage that is spirally-arranged in a basal rosette; and
2. 'LOCK02' exhibits long, broad foliage; and
3. 'LOCK02' exhibits light green foliage which is densely covered with prominent linear protuberances presenting as white raised ribs which transversely encircle both the adaxial and abaxial leaf surfaces.

BOTANICAL DESCRIPTION OF THE PLANT

Figure 1:
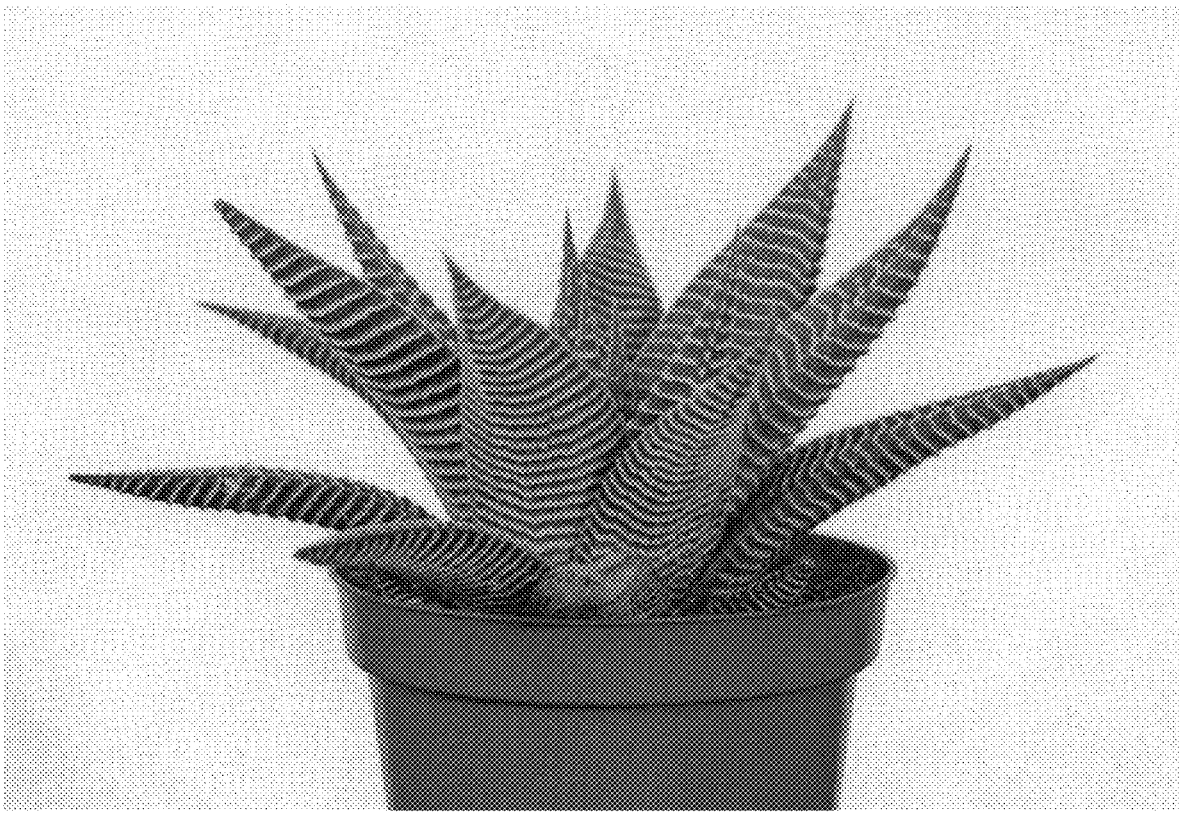
FIG. 1 illustrates, as nearly true as it is reasonably possible to make the same in color photographs of this type, an exemplary plant of 'LOCK02' grown in a commercial greenhouse in 's-Gravenzande, the Netherlands. This plant is approximately 12 months old, shown planted in an 8.5 cm container.
Figure 2:
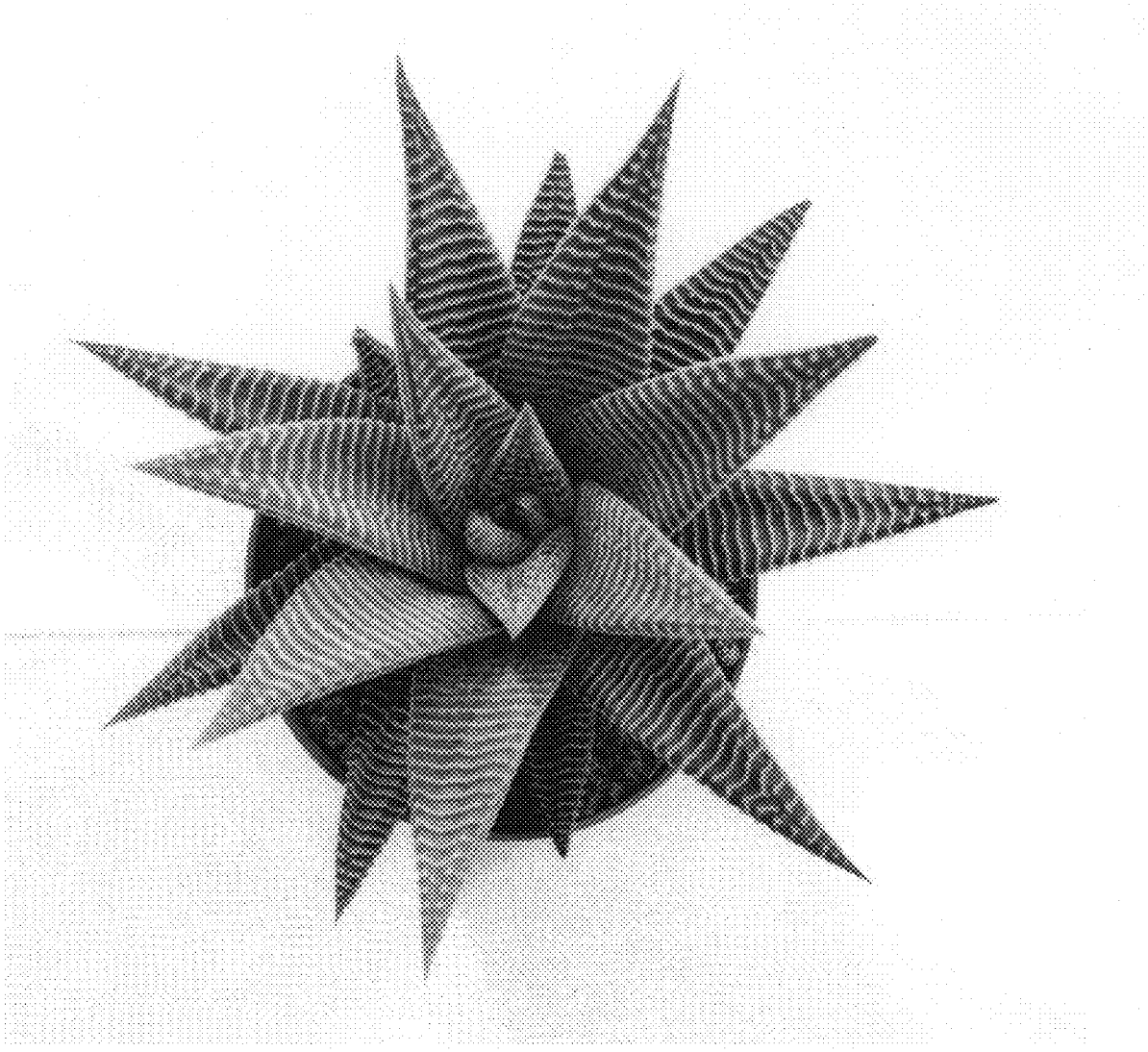
FIG. 2 illustrates, as nearly true as it is reasonably possible to make the same in color photographs of this type, the typical foliage arrangement of 'LOCK02'.
Figure 3:
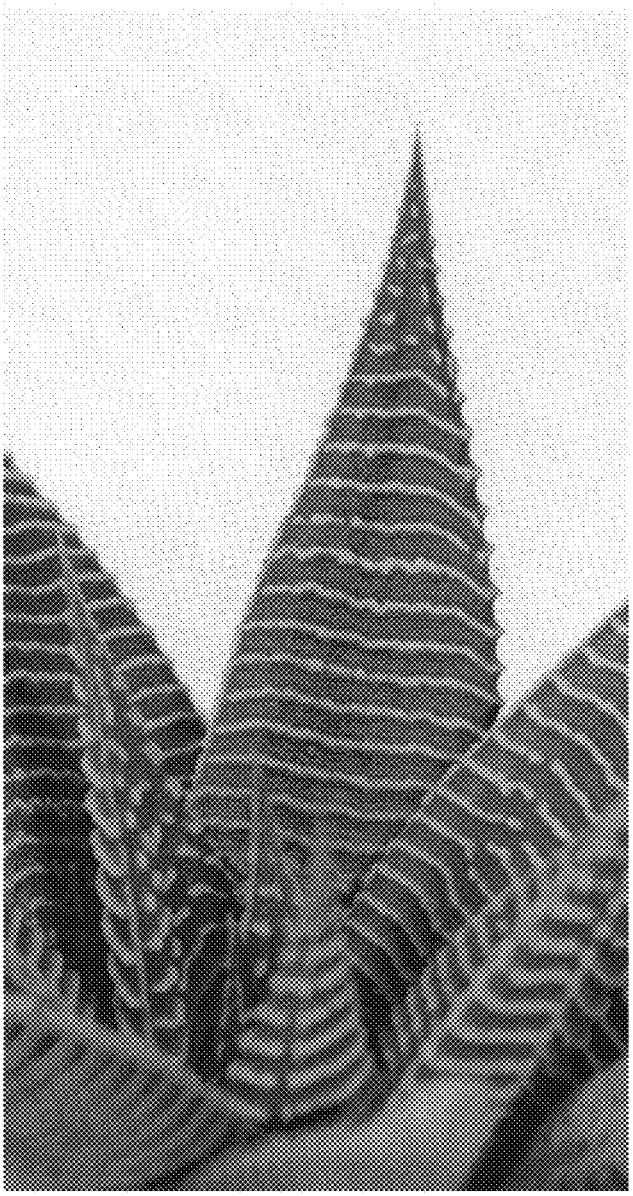
FIG. 3 illustrates, as nearly true as it is reasonably possible to make the same in color photographs of this type, the adaxial surface of the mature foliage 'LOCK02'.
Figure 4:
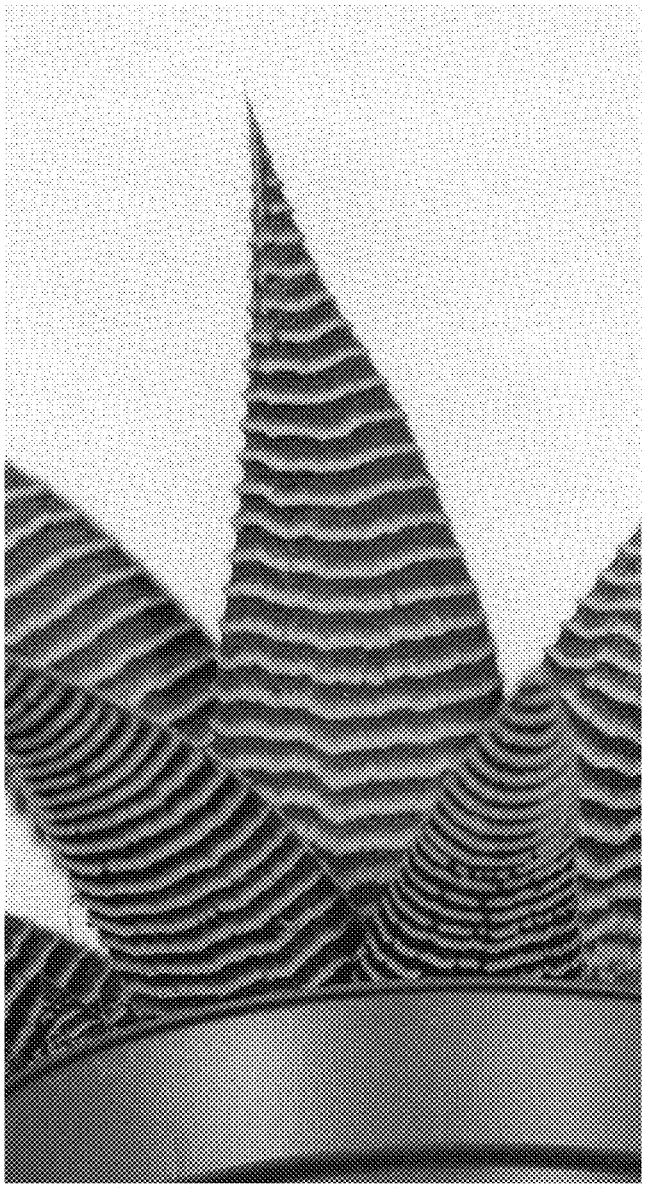
FIG. 4 illustrates, as nearly true as it is reasonably possible to make the same in color photographs of this type, the abaxial surface of the mature foliage 'LOCK02'.

The following observations and measurements made in October of 2019 describe averages from a sample set of six specimens of 12 months old 'LOCK02' plants grown in 8.5 cm nursery containers at commercial greenhouse in Heerhugowaard, the Netherlands. Plants were produced using conventional greenhouse production protocols for *Haworthia* plants which consisted of minimal overhead irrigation and regular fertilizer applications, and biological control measures against insect pests. Plants were grown under shade and no photoperiodic treatments or artificial light was given to the plants.

Those skilled in the art will appreciate that certain characteristics will vary with older or, conversely, with younger plants. 'LOCK02' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'LOCK02' and a comparison with the parent and closest known comparator is provided below.

Plant description:

*Growth habit*.—Succulent perennial with foliage growing in a stemless, non-branched basal rosette.

*Plant shape*.—Flattened globular.

*Height from soil level to top of foliar plane*.—7.3 cm.

*Plant spread*.—Average of 14.8 cm.

*Growth rate*.—Slow.

*Plant vigor*.—Moderately vigorous.

*Propagation*.—Type — Leaf cuttings. Time to initiate rooting — Approximately 10 days at 18 degrees Celsius. Crop time — From an in vitro micropropagule to a marketable plant in a 8.5 cm container takes approximately one year.

*Disease and pest resistance or susceptibility*.—Neither resistance nor susceptibility to typical *Aloe* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Spirally arranged in a rosette.

*Division*.—Simple.

*Attachment*.—Sessile.

*Quantity*.—24 leaves per rosette.

*Shape*.—Narrow deltoid to nearly lanceolate succulent foliage.

*Dimensions*.—8.0 cm long, 2.4 cm wide, and 0.7 cm thick, on average.

*Aspect*.—Very slightly concaved and slightly curled downward.

*Attitude*.—Juvenile foliage at the center of the rosette is held upright; foliage becomes progressively more relaxed towards the outer whorls of mature foliage, at an average angle of 45 degrees from horizontal.

*Apex*.—Narrow acute to long apiculate, with a very short soft mucronate tip.

*Base*.—Broad cuneate.

*Margin*.—Entire yet irregular due to the transverse rows of linear protuberances across the leaf surface which extend to the margins.

*Texture, adaxial surface*.—Glabrous and densely covered with conspicuous linear protuberances arranged in transverse rows across the leaf surface; an average of 22 row of protuberances per leaf; protuberances are approximately 0.1 cm high.

*Texture, abaxial surface*.—Glabrous and densely covered with conspicuous linear protuberances arranged in transverse rows across the leaf surface; an average of 22 row of protuberances per leaf; protuberances are approximately 0.1 cm high.

*Luster, adaxial surface*.—Matte.

*Luster, abaxial surface*.—Matte.

*Color*.—Juvenile foliage, adaxial surface — Green, nearest to RHS 138A; protuberances are colored white, nearest to RHS N155A. Juvenile foliage, abaxial surface — Green, nearest to RHS 138A; protuberances are colored white, nearest to RHS N155A. Mature foliage, adaxial surface — Green, nearest to in between RHS NN137A and NN137B; fading to a lighter shade of green towards the base, nearest to RHS 143B; linear protuberances are colored in between yellow-green and white, nearest to RHS 145D and N155A. Mature foliage, abaxial surface — Nearest to in between green and yellow-green, RHS 138A and 147A; linear protuberances are colored in between yellow-green and white, nearest to RHS 145D and N155A.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'LOCK02' differ from the parent, *Haworthia limifolia* 'LOCK01' (Community Plant Variety Rights grant number 28557), in the following characteristics described in Table 1 below.

TABLE 1

| Characteristic | 'LOCK02' | 'LOCK01' |
|---|---|---|
| Foliage shape. | Broader than 'LOCK01'. | Narrower than 'LOCK02'. |
| Foliage length. | Longer than 'LOCK01'. | Shorter than 'LOCK02'. |
| Foliage attitude. | More upright than 'LOCK01'. | More relaxed than 'LOCK02'. |

COMPARISONS WITH THE CLOSEST KNOWN COMPARATOR

Plants of the new cultivar 'LOCK02' differ from the closest known commercial comparator, *Haworthia maxima* 'AMIAL1601' (U.S. Plant Pat. No. 31,430), in the following characteristics described in Table 2 below.

TABLE 2

| Characteristic | 'LOCK02' | 'AMIAL1601' |
|---|---|---|
| General coloration of the mature foliage. | Lighter shade of green than 'AMIAL1601'. | Lighter shade of green than 'LOCK02'. |
| Foliar protuberances. | Conspicuous linear protuberances presenting as continuous raised ribs which transversely encircle both the adaxial and abaxial leaf surfaces. | Orbicular protuberances arranged in irregular, wavy transverse rows. |

TABLE 2-continued

| Characteristic | 'LOCK02' | 'AMIAL1601' |
|---|---|---|
| General coloration of the foliar protuberances. | In between yellow-green and white, generally appearing as white. | Light greyed-green. |

That which is claimed is:

1. A new and distinct variety of *Haworthia* plant named 'LOCK02', substantially as described and illustrated herein.

* * * * *